United States Patent
Rezai et al.

(10) Patent No.: US 9,539,425 B2
(45) Date of Patent: Jan. 10, 2017

(54) SYSTEMS AND METHODS FOR TREATING MEDICAL CONDITIONS BY STIMULATION OF MEDIAL THALAMIC REGION

(75) Inventors: Ali Rezai, Shaker Heights, OH (US); Nicholas Schiff, New York, NY (US); Scott Kokones, Cleveland, OH (US); Andre Machado, Beachwood, OH (US); Sierra Farris, Kirkland, WA (US)

(73) Assignees: Intelect Medical, Inc., Cleveland, OH (US); The Cleveland Clinic Foundation, Cleveland, OH (US); Cornell Research Foundation, Inc., Ithaca, NY (US)

( * ) Notice: Subject to any disclaimer, the term of this patent is extended or adjusted under 35 U.S.C. 154(b) by 1268 days.

(21) Appl. No.: 11/871,727

(22) Filed: Oct. 12, 2007

(65) Prior Publication Data
US 2008/0215101 A1 Sep. 4, 2008

Related U.S. Application Data

(60) Provisional application No. 60/851,296, filed on Oct. 13, 2006.

(51) Int. Cl.
*A61N 1/36* (2006.01)

(52) U.S. Cl.
CPC .......... *A61N 1/361* (2013.01); *A61N 1/36025* (2013.01); *A61N 1/36082* (2013.01); *A61N 1/36017* (2013.01)

(58) Field of Classification Search
CPC ................................................. A61N 1/36067
(Continued)

(56) References Cited

U.S. PATENT DOCUMENTS

| 5,716,377 A | 2/1998 | Rise et al. |
| 6,066,163 A | 5/2000 | John |

(Continued)

OTHER PUBLICATIONS

Lee, C.R., E.D. Abercrombie, and J.M. Tepper. "Pallidal Control of Substantia Nigra Dopaminergic Neuron Firing Pattern and Its Relation to Extracellular Neostriatal Dopamine Levels." Neuroscience 129.(2004): 481-489. ScienceDirect. Web. May 31, 2016.*

(Continued)

*Primary Examiner* — Allen Porter, Jr.
(74) *Attorney, Agent, or Firm* — Lowe Graham Jones PLLC; Bruce E. Black (57) ABSTRACT

A system for treating medical conditions by neuromodulation of one or more target sites in the nervous system. In certain embodiments, at least one of the target sites is the medial thalamic region, including the intralaminar nucleus and the adjacent white and grey matter. In certain embodiments, where there is more than one target site, the other target sites is elsewhere in the nervous system, including the globus pallidus interna, subthalamic nucleus, corpus callosum, cerebellum, cerebral cortex (including the premotor cortex, motor cortex, and sensory cortex), ventral striatum, lateral thalamus, substantia nigra, and pedunculopontine nuclei. The medical conditions include movement disorders or improvement of movement function, stroke, neuropsychiatric or neuropsychologic disorders, neurodevelopmental disorders, and pain. Methods for treating medical conditions by neuromodulation of the intralaminar nuclei either alone or in combination with another target site(s) is also provided.

15 Claims, 4 Drawing Sheets

(58) Field of Classification Search
USPC .............................................. 607/45, 48, 49
See application file for complete search history.

(56) References Cited

U.S. PATENT DOCUMENTS

| | | | |
|---|---|---|---|
| 6,167,311 | A | 12/2000 | Rezai |
| 6,463,328 | B1 | 10/2002 | John |
| 6,708,096 | B1 | 3/2004 | Frei et al. |
| 6,937,903 | B2 * | 8/2005 | Schuler et al. ................. 607/42 |
| 7,308,302 | B1 * | 12/2007 | Schuler et al. ................... 607/2 |
| 7,623,927 | B2 * | 11/2009 | Rezai ................ A61N 1/36082 607/2 |
| 2002/0151939 | A1 * | 10/2002 | Rezai ................ A61N 1/36082 607/40 |
| 2003/0097159 | A1 | 5/2003 | Schiff et al. |
| 2005/0010262 | A1 * | 1/2005 | Rezai ................ A61N 1/36071 607/46 |
| 2006/0095088 | A1 | 5/2006 | De Ridder |
| 2007/0000372 | A1 | 1/2007 | Rezai et al. |
| 2007/0078498 | A1 | 4/2007 | Rezai et al. |

OTHER PUBLICATIONS

Chinta, Shankar J., and Julie K. Andersen. "Dopaminergic Neurons." International Journal of Biochemistry and Cell Biology 5 (2005): 942. Academic OneFile. Web. May 31, 2016.*

Wagenbreth, Caroline, et al. "Deep Brain Stimulation of The Subthalamic Nucleus Modulates Reward Processing and Action Selection in Parkinson Patients." Journal of Neurology 262.6 (2015): 1541-1547. MEDLINE. Web. May 31, 2016.*

Cobb, W.S. and Abercrombie E.D. "Relative Involvement of Globus Pallidus and Subthalamic Nucleus in the Regulation of Somatodendritic Dopmaine Release in Substantia Nigra is Dopamine-Dependent". Neuroscience 119 (2003) 777-786.*

Winn, Philip. "How Best to Consider the Structure and Function of the Pedunculopontine Tegmental Nucleus: Evidence from Animal Studies". Journal of the Neurological Sciences 248 (2006) 234-250.*

* cited by examiner

| Location | Abbrev | Lateral X | AP Y | Sagittal Z | Interconnections |
|---|---|---|---|---|---|
| | | (all measurements are in mm relative to AC-PC Line) | | | |
| Intralaminar thalamic nuclei | ILN | | | | |
| Anterior ILN | | 7 to 13 | MCP to 10 anterior | 0 TO 13 | |
| Central Lateral (CL) | ILN-CL | | | | Prefrontal cortex, parietal cortex, visual association cortex, motor cortex |
| Paracentralis (Pc) | ILC-Pc | | | | Prefrontal cortex, orbitofrontal cortex, anterior cingulate |
| Paralamellar MD | ILC-Pl | | | | Prefrontal cortex, temporal association cortex, anterior parietal |
| Posterior ILN | | 5 to 10 | MCP: -5 to PC: -7 | 0 TO 13 | |
| Centromedian (Cm) | ILN-CM | | | | Prefrontal cortex, premotor cortex, parietal association cortex |
| Parafasicularis (Pf) | ILN-Pf | | | | Prefrontal cortex, premotor cortex, parietal association cortex |
| Midline ILN | | 2 to 8 | MCP to 10 anterior | 0 TO 13 | |
| Paraventricularis (Pv) | ILN-Pv | | | | Amygdala, Limbic System Hippocampus |
| Central Medial (CM) | | | | | Orbitofrontal, Limbic System, Hippocampus, Amygdala |
| Midline Nuclei | ILN-mid | | | | |

MCP  Mid commisural point (anterior is positive)
AC   Anterior commisure
PC   Posterior commisure
Sagittal  Superior is positive, inferior is negative

FIG.4

SYSTEMS AND METHODS FOR TREATING MEDICAL CONDITIONS BY STIMULATION OF MEDIAL THALAMIC REGION

CROSS-REFERENCES

This application claims priority to U.S. Provisional Application Ser. No. 60/851,296 (filed 13 Oct. 2006), which is incorporated by reference herein in its entirety.

TECHNICAL FIELD

The present invention relates to methods of treating medical conditions by electrical and/or chemical neuromodulation of target sites in the nervous system.

BACKGROUND

Neuromodulation involves an array of therapeutic approaches applied to the brain, cranial nerves, spinal cord and associated nerves and neural structures in the human body to treat various human disorders. Neuromodulation can involve lesioning, electrical stimulation/modulation and/or chemical stimulation/modulation including gene therapy and administration of stem cells. Electrical stimulation of neural tissue is becoming an increasingly preferred form of therapy for certain neurological conditions and disorders where existing therapies generate intolerable side effects, require repeated administration of treatment, or are simply ineffective in a subset of patients. Electrical stimulation provides distinct advantages over surgical lesioning techniques since electrical stimulation is a reversible and adjustable procedure that provides continuous benefits as the patient's disease progresses and the patient's symptoms evolve.

Currently, for deep brain targets, electrical stimulation of the subthalamic nucleus and the globus pallidus interna is approved for treatment of Parkinson's disease and electrical stimulation of the ventral intermediate nucleus is approved for treatment of essential tremor. However, there remains a need for other forms of neuromodulation to treat these and other disorders.

SUMMARY OF THE INVENTION

In one aspect, the present invention provides a system for treating a condition selected from the group consisting of: a movement disorder or improvement of movement function, stroke, neuropsychiatric or neuropsychologic disorder, neurodevelopmental disorder, and pain; wherein the system comprises: (a) a first therapy delivery device for positioning at a first target site, wherein the first target site is the medial thalamic region; and (b) a controller in communication with the first therapy delivery device for enabling the first therapy delivery device to deliver a stimulus to the first target site.

In another aspect, the present invention provides a system for treating a psychiatric condition comprising: (a) a first therapy delivery device for positioning at an intralaminar nuclei; (b) a second therapy delivery device for positioning at a target site in the nervous system, wherein the target site is the pre-frontal cortex, frontal lobe, dorsolateral frontal cortex, medial frontal cortex, temporal cortex, orbitofrontal cortex, subgenual cingulated cortex, amygdala, nucleus accumbens, or ventral striatum; and (c) a controller in communication with both the first therapy delivery device and the second therapy delivery device, wherein the controller delivers stimuli through the first therapy delivery device and second therapy delivery device.

In yet another aspect, the present invention provides a method of treating a condition selected from the group consisting of: a movement disorder or improvement of movement function, stroke, neuropsychiatric or neuropsychologic disorder, neurodevelopmental disorder, and pain; wherein the method comprises: delivering a first stimulus to a first target site, wherein the first target site is the intralaminar nuclei. In certain embodiments, the method may further comprise delivering a second stimulus to a second target site, wherein the second target site is not the intralaminar nuclei.

In yet another aspect, the present invention provides a method of treating a psychiatric condition comprising: (a) delivering a first stimulus to the intralaminar nuclei; and (b) delivering a second stimulus to a target site in the nervous system, wherein the target site is the pre-frontal cortex, frontal lobe, dorsolateral frontal cortex, medial frontal cortex, temporal cortex, orbitofrontal cortex, subgenual cingulated cortex, amygdala, nucleus accumbens, or ventral striatum.

DETAILED DESCRIPTION

Figure 1:
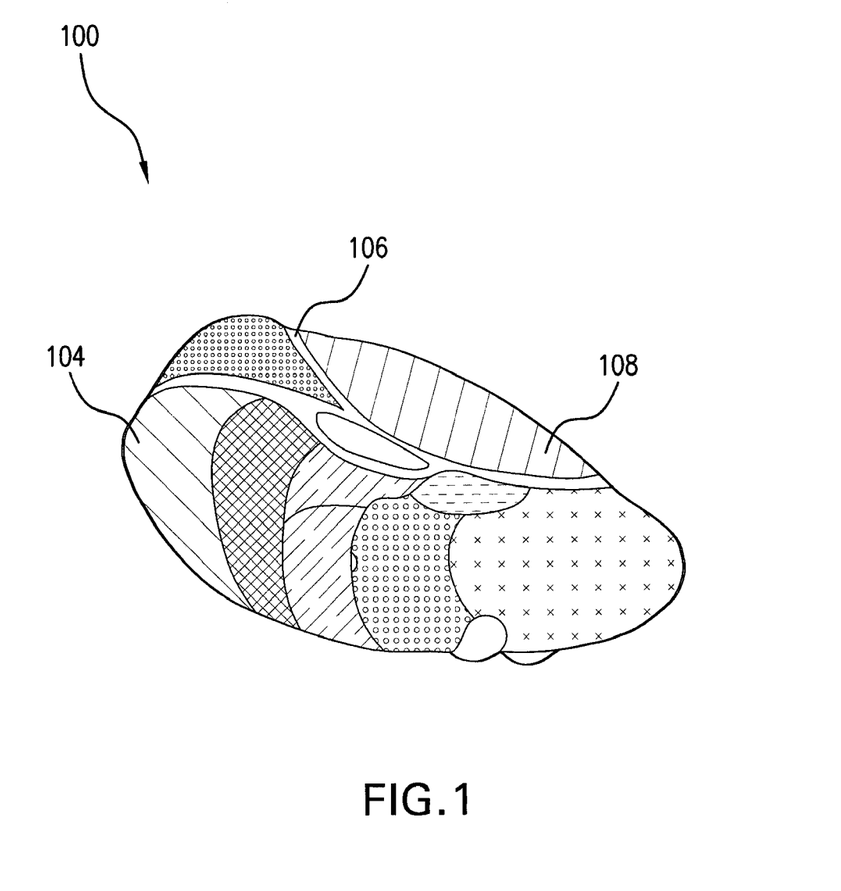
FIG. 1 illustrates the layout and orientation of the intralaminar nuclei, including the position of the related subdivisions and nuclei with respect to the thalamus.
Figure 4:
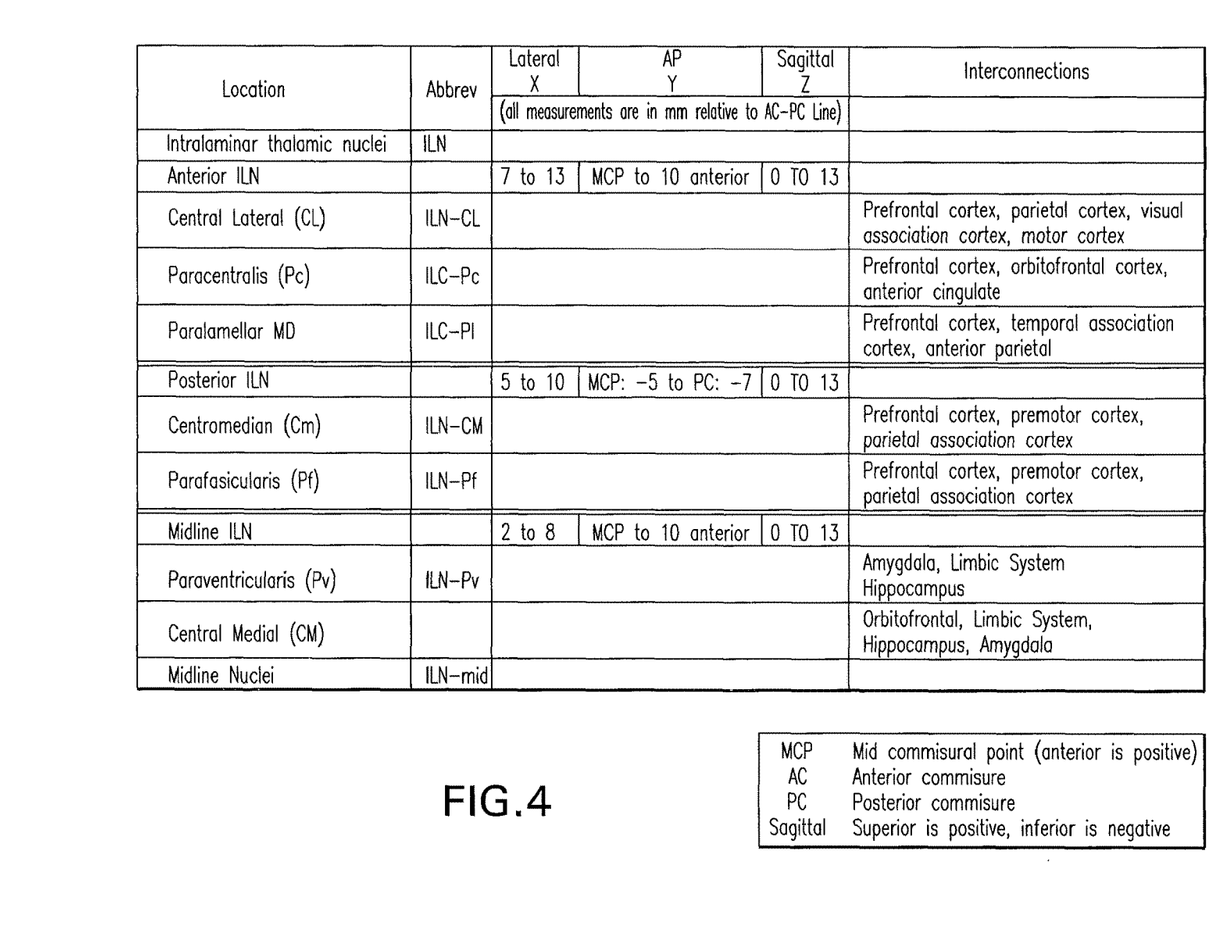
FIG. 4 shows a table with coordinates of various regions in the ILN.

In one aspect, the present invention provides a system for treating medical conditions (including neurologic and central nervous system (CNS) conditions) by neuromodulation of one or more target sites in the nervous system. In certain embodiments, at least one of the target sites is the medial thalamic region, including the intralaminar nucleus and the adjacent white and grey matter. The target site may include a single intralaminar nucleus or to any combination of intralaminar nuclei. Referring to FIG. 1, showing a thalamus 100, the intralaminar nuclei are a small set of nuclei located in the paramedian thalamus (dividing each of the lobes of the thalamus along a Y shaped vertical planar geometry which cuts through the posterior to anterior axis of each lobe). Within the intralaminar nuclei are the anterior 104, midline 106, and posterior 108 subgroups. The anterior subgroups 104 include the central lateral (CL) and paracentralis regions. The posterior subgroups 108 include the centromedian-parafascicularis complex (Cm-Pf). The midline 106 and other related subgroups include the centre medial (CeM) nuclei and the nucleus paraventricularis (Pv). Referring to FIG. 4, these structures and their X (medial-lateral), Y (anterior-posterior), and Z (superior-inferior) stereotactic coordinates with respect to the anterior commissure (AC) and the posterior commissure (PC) are identified.

Thalamic neurons can be distinguished into two chemically defined classes based on immunoreactivity to calcium-binding proteins. All thalamic nuclei contain calbindin-positive matrix cells, while only some nuclei also contain parvalbumin-positive core cells. Parvalbumin-positive cells project in a topographically ordered fashion to middle, or granular, layers of a single cortical field. In contrast, calbindin-positive matrix cells have wider and more diffuse projections terminating in the superficial layers of the cortex. Within the intralaminar nuclei there are regions in which core and matrix cells co-exist and others in which they are largely segregated. For example, the Cm-Pf nuclei contain an overwhelming population of parvalbumin-positive core cells and lack calbindin immunoreactivity, whereas calbindin-positive matrix cells predominate in the CL. Together, the thalamic matrix cells are positioned to influence long range cortico-cortico communication and in conjunction with core cells provide a co-incidence detection system to organize global cortico-thalamic synchrony.

As used herein, the term "treating" a medical condition encompasses therapeutically regulating, preventing, improving, alleviating the symptoms of, reducing the effects of and/or diagnosing the medical condition. As used herein, the term "medical condition" encompasses any condition, disease, disorder, function, abnormality, or deficit influenced by the neurologic system. The systems and methods of the present invention can be used to treat more than one medical condition concurrently.

Non-limiting examples of medical conditions that can be treated according to the systems and methods of the present invention include genetic, skeletal, immunological, vascular or hematological, muscular or connective tissue, neurological, ocular, auditory or vestibular, dermatological, endocrinological, olfactory, cardiovascular, genitourinary, psychological, gastrointestinal, respiratory/pulmonary, neoplastic, or inflammatory medical conditions. Further, the medical condition can be the result of any etiology including vascular, ischemic, thrombotic, embolic, infectious (including bacterial, viral, parasitic, fungal, abscessal), neoplastic, drug-induced, metabolic, immunological, collagenic, traumatic, surgical, idiopathic, endocrinological, allergic, degenerative, neurogenerative, craniofacial, congenital, or abnormal malformational causes.

The present invention also encompasses enhancing the therapeutic effects of other therapies, such as methods and systems working in conjunction with a pharmaceutical agent or other therapies to augment, enhance, improve, or facilitate other therapies (adjunctive therapies) as well as reducing/minimize and counteracting side effects, complications and adverse reactions for any therapies involved in treating the above-mentioned medical conditions. For example, the methods and systems of the present invention may be used in a patient with Parkinson's disease who is undergoing drug treatment. By using the methods and systems of the present invention in conjunction with the drug treatment, the drug dosage can be reduced.

With respect to treating neurological medical conditions, such medical conditions can involve any medical conditions related to the components of the nervous system such as, for example, the brain including the cerebellum, cerebello-thalamo-cortical pathways, cortico-ponto-ceraballar pathways, brain stem, pons, midbrain, medulla; the spinal cord; peripheral nerves; peripheral ganglia; and nerve plexuses. Non-limiting examples of neurological conditions include Alzheimer's disease, epilepsy, multiple sclerosis, ALS, Guillan Barre, stroke, cerebral palsy, intracerebral hemorrhage, dementia, vertigo, tinnitus, diplopia, cerebral vasospasm, aneurysm, atriovenous malformation, brain malformations, Parkinson's disorder, multi-system atrophy, olivopontocerebellar degeneration, familial tremor dystonia including cervical dystonia, torticollis, facial dystonia, blepharospasms, spasmodic dysphonia, radiculopathy, neuropathy, sleep disorders, disorders of temperature regulation in the body and extremities, postherpetic neuralgia involving the face, head, body or extremities. The neuropathy may be caused by fracture, crush injury, compressive injury, repetitive movement injury, diabetes, trauma, alcohol, infection, or hereditary. The sleep disorder may be sleep apnea, restless leg syndrome, narcolepsy, snoring, insomnia, and drowsiness.

In some instances, the medical condition may be a movement disorder which include or manifest as: ataxia, akinesia, athetosis, rigidity, spasms, ballismus, hemiballismus, bradykinesia, dystonia, chorea including Huntington's disease, multiple system atrophies (e.g., Shy-Drager syndrome), myoclonus, Parkinson's disease, progressive supranuclear palsy, restless leg syndrome and periodic limb movement disorder, tics, Tourette's syndrome, tremor (e.g., essential tremor, resting tremor), Wilson disease, or tardive dyskinesia. In some instances, the medical condition may be stroke due to cerebrovascular disease or a stroke due to other causes. The stroke may be ischemic or hemorrhagic.

With respect to treating cardiovascular medical conditions, such medical conditions can involve any medical conditions related to the components of the cardiovascular system such as, for example, the heart and aorta. Non-limiting examples of cardiovascular conditions include post-infarction rehabilitation, valvular disease, myocardial infarction, arrhythmia, heart failure, angina, microvascular ischemia, myocardial contractility disorder, cardiomyopathy, hypertension, orthostatic hypotension, dysautonomia, syncope, vasovagal reflex, carotid sinus hypersensitivity, and cardiac structural abnormalities such as septal defects and wall aneurysms. The cardiomyopathy may be caused by hypertension, alcohol, or by a congenital cause. The hypertension may be essential, primary, secondary, or renal.

With respect to treating psychiatric or psychologic medical conditions, non-limiting examples of such medical conditions include Tourette's syndrome, autism, mental retardation, stress, anxiety, apathy, arousal, depression, bipolar disorder, mania, schizophrenia, a personality disorder, a phobia, hallucinations, delusions, psychosis, addictions, and other affective disorders. The addiction may be to substances or behavior. The substance may be alcohol, cigarettes, or drugs.

With respect to treating gastrointestinal medical conditions, such medical conditions can involve any medical conditions related to the components of the gastrointestinal system such as, for example, the mouth, esophagus, stomach, small intestine, large intestine, rectum, liver, gall bladder, bile ducts, and pancreas. Non-limiting examples of gastrointestinal medical conditions include hepatic failure, hepatitis, cirrhosis, dumping syndrome, cirrhosis, gastric or duodenal ulcer, irritable bowel syndrome, inflammatory bowel disease, colitis, diverticulosis, diverticulitis, emesis, hyper emesis gravidum, bowel incontinence, constipation, diarrhea, abdominal cramps, gastro esophageal reflux, esophageal dysmotility, gastric dysmotility, cholecystitis, gall stones, pancreatic insufficiency, gas, bloating, and gastritis.

With respect to treating respiratory/pulmonary medical conditions, such medical conditions can involve any medical conditions related to the components of the respiratory system such as, for example, the trachea, bronchus, bronchioles, alveoli, lungs, and capillaries. Non-limiting examples of respiratory medical conditions include reactive airway disease, asthma, emphysema, COPD, silicosis, sleep apnea, and cystic fibrosis.

The systems of the present invention comprise one or more therapy delivery devices that can be positioned at target sites to deliver a stimulus to the target sites. At least one of the target sites is the intralaminar nuclei. In certain instances, the system may comprise a single therapy delivery device. In other instances, the system may comprise two or more therapy delivery devices, wherein each may be directed to a different target site. Where there is more than one target site, the other target sites may be elsewhere in the nervous system, including the globus pallidus interna, subthalamic nucleus, corpus callosum, cerebellum, cerebral cortex (including the premotor cortex, motor cortex, and sensory cortex), ventral striatum, lateral thalamus, substantia nigra, and pedunculopontine nuclei.

In certain embodiments, systems are provided to treat movement disorders by stimulating an intralaminar nucleus and the globus pallidus interna and/or the subthalamic nucleus. In certain embodiments, systems are provided to treat stroke (e.g., during rehabilitation therapy) by stimulating an intralaminar nucleus and the corpus callosum, the cerebellum and/or the cortex. In certain embodiments, systems are provided to treat psychiatric disorders by stimulating an intralaminar nucleus and the visual cortex and/or the ventral striatum. In certain embodiments the psychiatric disorder is depression and the target sites may be a site in the intralaminar nucleus, pre-frontal cortex, frontal lobe, dorsolateral frontal cortex, medial frontal cortex, temporal cortex, orbitofrontal cortex, subgenual cingulated cortex, amygdala, nucleus accumbens, or ventral striatum. In other embodiments, the psychiatric disorder is an attention, mood, anxiety, apathy, arousal, connectivity or addiction disorder and the target sites are an intralaminar nucleus and the ventral striatum.

The therapy delivery device may be used to deliver electrical stimulation, bioactive agents (e.g., drugs for neuromodulation), or combinations thereof. As such, the therapy delivery device may have an electrode, a catheter or drug port for delivering a bioactive agent, or combinations thereof. Where the therapy delivery device is an electrode, the stimulus being delivered are electrical signals. In some cases, the electrical signals are of sufficient strength to induce a neurophysiological response, but not enough to cause tissue damage. In other cases, the electrical signals may be of sufficient strength to cause tissue damage (e.g., tissue lesioning or ablation). Where the therapy delivery device is a drug port, the stimulus being delivered are bioactive agents (e.g., providing chemical signals). The therapy delivery device is connected to a controller via an electrical stimulation lead (for an electrode) or an infusion catheter (for a drug port). The therapy delivery device has a configuration that allows the therapy deliver device to maximize contact with and optimally deliver stimulus to the target site.

In embodiments where the therapy delivery device is an electrode, the electrical stimulation lead may have a lead proximal end, a lead body, and a lead distal end. The lead distal end may comprise at least one electrode. The at least one electrode can be a plurality of electrodes. The electrodes at the lead distal end can be either monopolar, bipolar, or multipolar, and can operate as a cathode or an anode. The electrode can be composed of but not limited to activated iridium, rhodium, titanium, or platinum and combinations of said materials. The electrode may be coated with a thin surface layer of iridium oxide, titanium nitride or other surface modifications to enhance electrical sensitivity. The stimulation lead can also comprise carbon, doped silicon, or silicon nitride. Each lead distal end can be provided with a biocompatible fabric "collar" or band about the electrode periphery to allow it to be more readily sutured or glued into place (for electrodes to be secured in this manner). The stimulation lead may be placed permanently or temporarily in the target site to provide chronic or acute neuromodulation of the target site.

The controller is used to operate and supply power to the therapeutic delivery device and enable the therapy delivery device to deliver a stimulus (such as an electrical signal or a chemical signal) to the target site. The controller may be powered by a battery, an external power supply, a fuel cell, or a battery pack for external use. The controller may also be integral with the therapeutic delivery device (such as a single-unit stimulation lead/power generator). When the therapeutic delivery device is a stimulation lead, the controller may change the output to the electrode by way of polarity, pulse width, amplitude, frequency, voltage, current, intensity, duration, wavelength, and/or waveform. When the therapeutic delivery device is a drug port, the controller may change its output such that a pump, pressure source, or proportionally controlled orifice increases or decreases the rate at which the pharmaceutical is delivered to the target site. The controller may operate any number or combination of electrodes, and pharmaceutical delivery devices. For example, the controller may be connected to stimulation leads and a peristaltic pump for delivering a pharmaceutical to the target site near the stimulation leads. The controller may be implanted within the patient or it may be positioned by leads outside of the patient. A portion of the control system may be external to the patient's body for use by the attending physician to program the implanted controller and to monitor its performance. This external portion may include a programming wand which communicates with the implanted controller by means of telemetry via an internal antenna to transmit parameter values (as may be selectively changed from time to time by subsequent programming) selected at the programmer unit, such as a computer. The programming wand also accepts telemetry data from the controller to monitor the performance of the therapy delivery device.

In embodiments where the controller enables a stimulation lead to deliver an electrical signal to the target site, the electrical signal may be episodic, continuous, phasic, in clusters, intermittent, upon demand by the patient or medical personnel, or preprogrammed to respond to a sensor. Preferably, the oscillating electrical signal is operated at a voltage between about 0.1 microvolts to about 50 V. More preferably, the oscillating electrical signal is operated at a voltage between about 1 V to about 15 V. For microstimulation, it is preferable to stimulate within the range of 0.1 microvolts to about 1 V. Preferably, the electric signal source is operated at a frequency range between about 2 Hz to about 10,00 Hz. More preferably, the electric signal source is operated at a frequency range between about 2 Hz to about 200 Hz. Preferably, the pulse width of the oscillating electrical signal is between about 10 microseconds to about 1,000 microseconds. More preferably, the pulse width of the oscillating electrical signal is between about 50 microseconds to about 2000 microseconds. Preferably, the application of the oscillating electrical signal is: monopolar when the stimulation lead is monopolar; bipolar when the stimulation lead is bipolar; and multipolar when the stimulation lead is multipolar. The waveform may be, for example, biphasic, square wave, sine wave, or other electrically safe and feasible combinations. In some cases, where the therapy delivery device provides both electrical stimulation and chemical modulation, the pulses (single or paired) may be coordinated with the chemical infusion. In certain instances, the waveform may be neurally coded waveforms that imitate the electrical signals that are naturally produced by the body. In some cases, neurally coded waveforms may be pre-recorded, such as those obtained by in vivo recordings from human subjects or animals as described in U.S. patent application Ser. No. 11/522,029 (filed 15 Sep. 2006) and Ser. No. 11/404,006 (filed 13 Apr. 2006), both entitled "System and Method for Providing a Waveform for Stimulating Biological Tissue." In some cases, the pre-recorded waveforms may be obtained from a healthy or at least partially functioning thalamus, such as the contralateral thalamus from the same patient or a thalamus from another person. Using additional stimulation leads, electrical stimulation may be applied to multiple target sites. The controller may coordinate or synchronize the electrical stimulation of the multiple target sites. For example, the electrical stimulation to multiple target sites may be delivered simultaneously, sequentially, in an alternating fashion, or with time-delay.

In embodiments where the controller enables a drug port to deliver a bioactive agent (such as a chemical signal) to the target site, a bioactive agent may be delivered to the target site prior to, concurrent with, subsequent to or instead of electrical neuromodulation. The bioactive agent may be a neurotransmitter mimick; neuropeptide; hormone; pro- hormone; antagonist, agonist, reuptake inhibitor, or degrading enzyme thereof; peptide; protein; therapeutic agent; amino acid; nucleic acid; stem cell or any combination thereof and may be delivered by a slow release matrix or drug pump. The delivery of the bioactive agent maybe continuous, intermittent, chronic, phasic, or episodic.

The present invention also provides systems for treating medical conditions incorporating a closed-loop feedback mechanism. Specifically, in such embodiments, the system comprises a therapy delivery device for applying a therapy signal (which can be an electrical signal or a chemical signal) to the intralaminar nuclei. The system further comprises a sensor for detecting a bodily activity associated with the medical condition and for generating a sensor signal. The system also includes a controller in communication with the therapy delivery device for activating the therapy delivery device to initiate application of the therapy signal to the target site or to adjust application of the therapy signal to the target site in response to the sensor signal. The bodily activity to be detected by the sensor is any characteristic or function of the body including bodily organs, such as mechanical, motion, electrical, or chemical activity and includes, for example, gastrointestinal function including gastric acid, intestinal motility, and peristalsis; temperature; respiratory function; heart rate; capillary pressure; venous pressure; perfusion; blood gases such as carbon dioxide including partial pressure of carbon dioxide; oxygenation including blood oxygenation levels, oxygen saturation levels partial pressure of oxygen, oxygen consumption, oxygen pressure; water pressure; nitrogen pressure; carbon dioxide pressure in the tissue; circulation (including blood and lymphatic); electrolyte levels in the circulation/tissue; diffusion or metabolism of various agents and molecules (such as glucose); neurotransmitter levels; body temperature regulation; blood pressure; blood viscosity; metabolic activity; cerebral blood flow; pH levels; vital signs; galvanic skin responses; perspiration; electrocardiogram; electroencephalogram; action potential conduction; chemical production; body movement including limb movement, posture, and gait; response to external stimulation; cognitive activity; dizziness; pain; flushing; motor activity including muscle tone; visual activity; speech; balance; diaphragmatic movement; chest wall expansion; concentration of certain biological molecules/substances in the body such as, for example, glucose, liver enzymes, electrolytes, hormones, creatinine, medications, concentration of various cells, platelets, or bacteria. These bodily activities can be measured utilizing a variety of methods including but not limited to chemical analysis, mechanical measurements, laser, and fiber-optic analysis.

In specific embodiments, the system may further comprise one or more sensors. The sensors may be located on or within the body and detect mechanical, motion, electrical, and/or chemical activity. Such activity may be detected by sensors located within the target site, proximal to the target site, or distal to the target site, whether in or outside the nervous system. Examples of electrical activity detected by sensors located within or proximal to the target site include sensors that measure neuronal electrical activity, such as the electrical activity characteristic of the signaling stages of neurons (i.e. synaptic potentials, trigger actions, action potentials, and neurotransmitter release) at the target site and by afferent and efferent pathways and sources that project to and from or communicate with the target site. For example, the sensors can measure, at any signaling stage, neuronal activity of any of the extensive connections of the target site. In particular, the sensors may detect the rate and pattern of the neuronal electrical activity to determine the electrical signal to be provided to the lead. Examples of chemical activity detected by sensors located within or proximal to the target site include sensors that measure neuronal activity, such as the modulation of neurotransmitters, hormones, pro-hormones, neuropeptides, peptides, proteins, electrolytes, or small molecules by the target site and modulation of these substances by afferent and efferent pathways and sources that project to and from the target sites or communicate with the target sites. With respect to detecting electrical or chemical activity in the nervous system, such sensors could be placed in the brain, the spinal cord, cranial nerves, and/or spinal nerves. For example, the sensors could be placed in the intralaminar nuclei to sense neuronal electrical activity. In certain embodiments relating to treating movement disorders, the activity in the intralaminar nuclei is sensed and the globus pallidus and/or subthalamic nucleus is stimulated. Sensors placed in the brain are preferably placed in a layer-wise manner. For example, a sensor could be placed on the scalp (i.e. electroencephalogram), in the subgaleal layer, on the skull, in the dura mater, in the sub dural layer and in the parenchyma (i.e. in the frontal lobe, occipital lobe, parietal lobe, temporal lobe) to achieve increasing specificity of electrical and chemical activity detection. The sensors could measure the same types of chemical and electrical activity as the sensors placed within or proximal to the target site as described above. With respect to detecting mechanical, motion, electrical, or chemical activity by sensors located outside the nervous system, such sensors may be placed in venous structures and various organs or tissues of other body systems, such as the endocrine system, musculoskeletal system, respiratory system, circulatory system, urinary system, integumentary system, and digestive system or such sensors may detect signals from these various body systems. For example, the sensor may be an external sensor such as a pulse oximeter, or an external blood pressure, heart, and respiratory rate detector. In another example, the sensors may be motion detectors attached to a body limb for detecting tremors, abnormal gait, or other abnormal movement. All the above-mentioned sensing systems may be employed together or any combination of less than all sensors may be employed together.

After the sensor(s) detect the relevant bodily activity associated with the medical condition, according to the systems of the present invention, the sensors generate a sensor signal. The sensor signal is processed by a sensor signal processor, which in this embodiment is part of the controller. The controller generates a response to the sensor signal by activating the therapy delivery device to initiate application of the therapy signal or to adjust application of the therapy signal to the target site. The therapy deliver device then applies the therapy signal to the target site. In embodiments where the therapy delivery device is a stimulation lead and the therapy signal is an electrical signal, activating the stimulation lead to adjust application of the electrical signal includes terminating, increasing, decreasing or changing the rate or pattern of a pulsing parameter of the electrical stimulation and the electrical signal can be the respective termination, increase, decrease or change in rate or pattern of the respective pulsing parameter. In embodiments where the therapy delivery device is a drug port and the therapy signal is a chemical signal, activating the drug port to adjust application of the chemical signal can be an indication to terminate, increase, decrease or change the rate or pattern of the amount or type of chemical agent administered, and the chemical signal can be the respective initiation, termination, increase, decrease or change in the rate or pattern of the amount or type of chemical agent administered. The processing of closed-loop feedback systems for electrical and chemical stimulation are described in more detail in respective U.S. Pat. Nos. 6,058,331 and 5,711,316, both of which are incorporated by reference herein.

Figure 2:
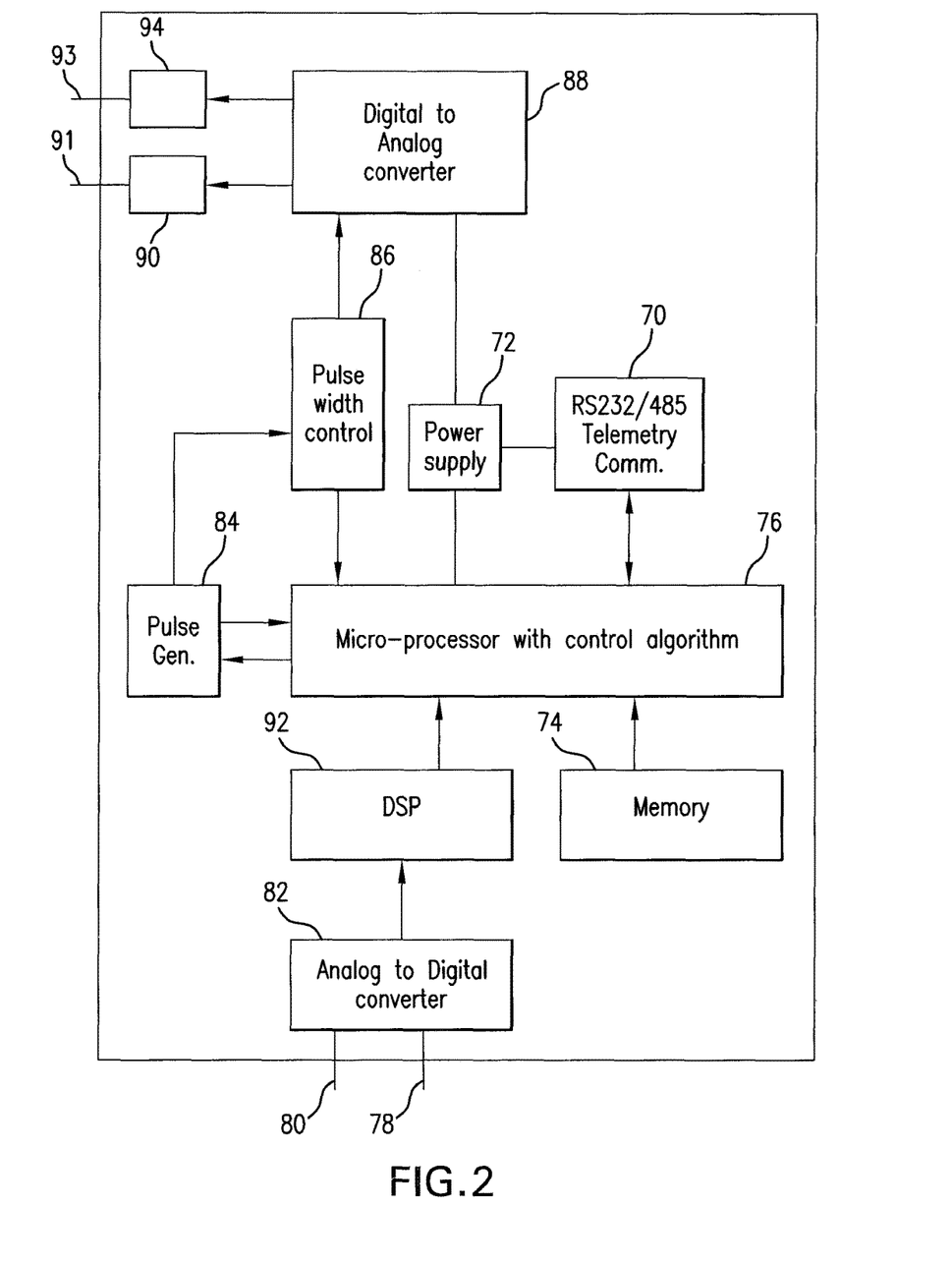
FIG. 2 is a schematic illustration of the components which may be used in a controller of the present invention.

Closed-loop electrical stimulation, according to the present invention can be achieved by a modified form of an implantable SOLETRA, KTNETRA, RESTORE, or SYNERGY signal generator available from Medtronic, Minneapolis, Minn., as disclosed in U.S. Pat. No. 6,353,762, the teaching of which is incorporated herein in its entirety, a controller as described in FIG. 2, or utilization of CIO DAS 08 and CIO-DAC 16 1 processing boards and an IBM compatible computer available from Measurement Computing, Middleboro, Mass. with Visual Basic software for programming of algorithms. With reference to FIG. 2 an illustration of a non-limiting example of a controller comprising a microprocessor 76 such as an MSP430 microprocessor from Texas Instruments Technology, analog to digital converter 82 such as AD7714 from Analog Devices Corp., pulse generator 84 such as CD 1877 from Harris Corporation, pulse width control 86, lead driver 90, digital to analog converter 88 such as MAX538 from Maxim Corporation, power supply 72, memory 74, and communications port or telemetry chip 70 are shown. Optionally, a digital signal processor 92 is used for signal conditioning and filtering. Input leads 78 and 80 and output lead to lead (therapeutic delivery device) 91 and drug delivery device (therapeutic deliver device) 93 are also illustrated. Additional stimulation leads, sensors, and therapeutic delivery devices may be added to the controller as required. As a non-limiting example, inputs from sensors, such as heart rate and blood pressure sensors, are input to analog to digital converter 82. Microprocessor 76 receiving the sensor inputs uses algorithms to analyze the biological activity of the patient and using PTD, "fuzzy" logic, or other algorithms, computes an output to pulse generator and/or drug delivery device drivers 90 and 94, respectively, to neuromodulate the target site where the therapeutic delivery devices are placed. The output of analog to digital converter 82 is connected to microprocessor 76 through a peripheral bus including address, data and control lines. Microprocessor 76 processes the sensor data in different ways depending on the type of transducer in use. When the signal on the sensor indicates biological activity outside of threshold values, for example elevated blood pressure or heart rate, programmed by the clinician and stored in a memory, the electrical signal applied through output drivers 90 and 94 of the controller will be adjusted. The output voltage or current from the controller are then generated in an appropriately configured form (voltage, current, frequency), and applied to the one or more therapeutic delivery devices placed at the target site for a prescribed time period to reduce elevated blood pressure or heart rate. If the patient's blood pressure or heart rate as monitored by the system is not outside of the normal threshold limits (hypotensive or hypertensive, bradycardic or tachycardic), or if the controller output (after it has timed out) has resulted in a correction of the blood pressure or heart rate to within a predetermined threshold range, no further electrical signal is applied to the target site and the controller continues to monitor the patient via the sensors. A block diagram of an algorithm which may be used in the present invention is shown in FIG. 3.

Figure 3:
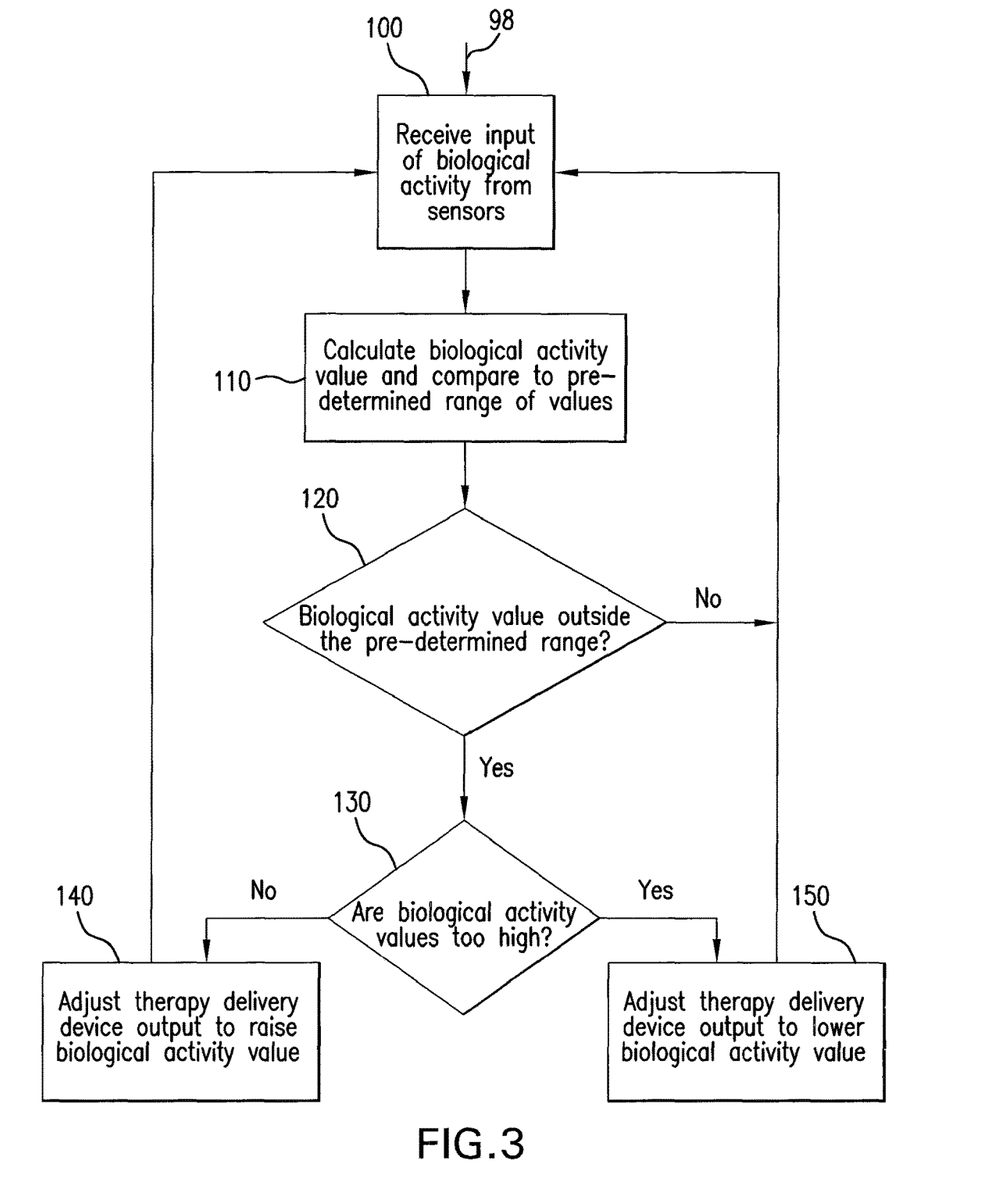
FIG. 3 is a block diagram of an algorithm to determine action which may be taken by the controller microprocessor in response to sensor input.

Referring to FIG. 3, suitably conditioned and converted sensor data 98 is input to the algorithm in block 100. The program computes at least one value of at least one biological activity related to a particular medical condition such as, for example, blood pressure, heart rate, or cardiac output, and compares the measured value of the biological activity to a pre-determined range of values, which is determined in advance to be the desired therapeutic range of values. This range is programmed into the microprocessor via the telemetry or communications port of the controller. The algorithm compares, 110, and then determines whether or not the measured value lies outside the pre-determined range of values, 120. If the measured biological activity value is not outside the pre-determined range of values, the program continues to monitor the sensors and reiterates the comparison part of the algorithm. If the measured biological value is outside of the pre-determined range of values, a determination or comparison is made, 130, as to whether the value is too high or too low compared with the pre-determined range. If the biological activity value is too high, an adjustment to the therapeutic delivery device is made, 150, to lower the biological activity value of the patient by calculating an output signal for pulse generator or drug delivery device to deliver a sufficient amount of the pharmaceutical or electrical stimulation to lower the biological activity of the patient. The algorithm continues to monitor the biological activity following the adjustment. If the biological activity value is too low then an adjustment to the therapeutic delivery device is made, 140, to raise the biological activity value by calculating an output signal for the pulse generator or drug delivery device to deliver a sufficient amount of a pharmaceutical or electrical stimulation to raise the biological activity value of the patient. The algorithm continues to monitor the biological activity of the patient, 100, following the adjustment. The amount of adjustment made may be determined by proportional integral derivative algorithms of by implementation of "fuzzy" logic rules.

With respect to the control of specific electrical parameters, the stimulus pulse frequency may be controlled by programming a value to a programmable frequency generator using the bus of the controller. The programmable frequency generator provides an interrupt signal to the microprocessor through an interrupt line when each stimulus pulse is to be generated. The frequency generator may be implemented by model CDP1878 sold by Harris Corporation. The amplitude for each stimulus pulse may be programmed to a digital to analog converter using the controller's bus. The analog output is conveyed through a conductor to an output driver circuit to control stimulus amplitude. The microprocessor of the controller may also program a pulse width control module using the bus. The pulse width control provides an enabling pulse of duration equal to the pulse width via a conductor. Pulses with the selected characteristics are then delivered from signal generator through a cable and lead to the target site or to a device such as a proportional valve or pump. For some types of sensors, a microprocessor and analog to digital converter will not be necessary. The output from sensor can be filtered by an appropriate electronic filter in order to provide a control signal for signal generator. An example of such a filter is found in U.S. Pat. No. 5,259,387 ("Muscle Artifact Filter") issued to Victor de Pinto on Nov. 9, 1993, incorporated herein by reference in its entirety.

At the time the therapy delivery device is implanted, the clinician programs certain key parameters into the memory of the implanted device via telemetry. These parameters may be updated subsequently as needed. The clinician may also program the range of values for pulse width, amplitude and frequency which the therapy delivery device may use to optimize the therapy. The clinician may also choose the order in which the parameter changes are made. Alternatively, the clinician may elect to use default values or the microprocessor may be programmed to use "fuzzy" logic rules and algorithms to determine output from the therapeutic delivery device to the patient based on sensor data and threshold values for the biological activity.

Although the application of sensors to detect bodily activity are part of embodiments of systems of the present invention, the present invention also contemplates the relevant bodily activity to be detected without sensors. In such cases, the neuromodulation parameters are adjusted manually in response to the clinical course of the disease or reporting by the patient.

In another aspect, the present invention provides a method of stabilizing and/or optimizing bodily functions, augmenting function, or treating the various medical conditions listed herein. In certain embodiments, the method can be used to augment immune response, which can involve any of the various components of the immune system such as the white blood cells, spleen, or thymus. In some cases, immune response can be augmented to treat an immunological medical condition, which can include immuno-suppressed states, immuno-compromised states, auto-immune disorders, drug-related allergy, an environmental allergy, or hypogamaglobunimia.

The method comprises delivering a stimulus to one or more target sites in the nervous system. In certain embodiments, at least one of the target sites is the medial thalamic region, including the intralaminar nucleus and the adjacent white and grey matter. The target site may include a single intralaminar nuclei or to any combination of intralaminar nuclei. Other target sites may be elsewhere in the nervous system, including the globus pallidus interna, corpus callosum, cerebellum, cerebral cortex (including the premotor cortex, motor cortex, and sensory cortex), ventral striatum, lateral thalamus, substantia nigra, and pedunculopontine nuclei.

The stimulus may be delivered by positioning one or more therapy delivery devices at the one or more target sites. The therapy delivery device may be activated to apply a therapy signal (electrical and/or chemical signal) to the target site. This method can be performed in the operating room, procedure room or imaging (MRI, CT, X-ray, fluoroscopy or optical imaged guided) suite. The procedures can be carried out peri-operative or post-operative to a surgical operation as well as in an intensive care unit and any other commonly utilized in-patient and out-patient capacities. Preferably, the surgical operation includes procedures that may require heart bypass equipment, procedures that may require a respiratory ventilator, or surgeries where intravenous medications are used during and after surgery to influence cardiac and/or pulmonary function. In an alternative embodiment, this method is performed in a non-surgical setting where intravenous medications are used for sedation, analgesia and to stabilize cardiac function, such as in the setting of myocardial infarction.

When two or more target sites are being stimulated, stimulation may be coordinated or synchronized. For example, the stimulation in one target site and another target site may be simultaneous, alternating, or time-delayed.

Neuromodulation of the target sites of the present invention can be temporary or short term (e.g., within seconds, minutes, hours, days, or less than 10 days); intermediate (10-30 days); or chronic (greater than 30 days). Further, the target sites can be accessed using any of the current approaches used by neurosurgeons, spinal surgeons, cardio-thoracic surgeons, vascular surgeons, abdominal surgeons, GU surgeons, ENT surgeons, plastic surgeons, interventional radiologists including endovascular neuroradiologists, neurologists, pain management specialists, rehabilitation and physical therapy specialists, and anesthesiologists. The procedures involves direct and in-direct placement of the therapy delivery device. This can be achieved using percutaneous, endoscopic, intravascular, or open surgical approach. Furthermore all these approaches can be guided by imaging means of MRI/CT/X-ray/fluoroscopy/optical imaging.

The influence of the neuromodulation of the systems and methods of the present invention can be manifested as changes in biological activity. For example, with respect to movement disorders or conditions, such changes can include reduction in tremors, improved postural stability, improved limb movement, improved gait, reduced extrapyramidal effects, reduced spasms, improved muscle control, improved speech, or improved alertness. In another example, with respect to treating cardiovascular medical conditions, such changes include changes in heart rate, heart rhythm, blood flow to the heart and cardiac contractility. These changes are reflected physiologically by parameters such as, for example, heart rate, blood pressure, cardiac output, stroke volume, pulmonary wedge pressure, and venous pressure, all of which can be measured. Preferably, the neuromodulation allows for selective changes in one or more aspects of the target organ whose function is being influenced without influencing or minimally influencing other functions of the target organ. For example, cardiac function may be selectively influenced by varying the parameters of stimulation such that cardiac contractility is affected but not heart rate.

The influence of neuromodulation of this method of the present invention on the respiratory system, for example, can be manifested in respiratory rate, changes in elasticity of the lung tissue, changes in diameter of the bronchioles and other structures in the respiratory branches, perfusion and diffusion of blood and its products at the level of the alveoli and blood flow to the lungs. These changes are reflected physiologically by parameters such as, for example, respiratory rate, pH of blood, bicarbonate level, ventilatory volume, lung capacity, and blood oxygenation.

The foregoing description has been set forth merely to illustrate the invention and is not intended as being limiting.

Each of the disclosed aspects and embodiments of the present invention may be considered individually or in combination with other aspects, embodiments, and variations of the invention. In addition, unless otherwise specified, none of the steps of the methods of the present invention are confined to any particular order of performance. Modifications of the disclosed embodiments incorporating the spirit and substance of the invention may occur to persons skilled in the art and such modifications are within the scope of the present invention. For example, although methods of treating specific medical conditions are described with respect to electrical and chemical neuromodulation, other modes of neuromodulation can be used such as light, magnetism, sound, pressure, and heat/cold. Furthermore, all references cited herein are incorporated by reference in their entirety.

We claim:

1. A method of treating a condition selected from the group consisting of: a movement disorder or improvement of movement function, wherein the method comprises:
    sensing neuronal electrical activity from a sensor placed in intralaminar nuclei of a patient;
    delivering, in response to the sensing, a first stimulus to a first target site that is the intralaminar nuclei of the patient; and
    delivering a second stimulus to a second target site selected from the group consisting of a globus pallidus interna, lateral thalamus, substantia nigra, pedunculopontine nuclei, premotor cortex, motor cortex, and sensory cortex, wherein the condition being treated is a movement disorder or improvement of movement function affected by the movement disorder.

2. The method of claim 1, wherein the second target site is selected from the group consisting of the pedunculopontine nuclei, premotor cortex, motor cortex, and sensory cortex.

3. The method of claim 1, further comprising positioning a first therapy delivery device at the intralaminar nuclei, and delivering the first stimulus through the first therapeutic delivery device.

4. The method of claim 3, wherein the first therapy delivery device is a drug port.

5. The method of claim 4, wherein the first therapy delivery device is an electrode.

6. The method of claim 5, wherein delivering the first stimulus through the electrode causes localized tissue damage at the first target site.

7. The method of claim 4, wherein sensing neuronal electrical activity comprises sensing the neuronal electrical activity using the first therapy delivery device positioned at the intralaminar nuclei.

8. The method of claim 1, wherein the movement disorder is selected from the group consisting of Parkinson's disorder, dystonia, tremor, and spasticity.

9. The method of claim 1, wherein the movement function is postural stability, gait, limb movement, balance, speech, swallowing, control of axial musculature, or autonomic control.

10. The method of claim 1, wherein the delivery of the first stimulus and delivery of the second stimulus are coordinated.

11. The method of claim 10, wherein the delivery of the first stimulus and delivery of the second stimulus are simultaneous.

12. The method of claim 10, wherein the delivery of the first stimulus and delivery of the second stimulus are alternating.

13. The method of claim 10, wherein the delivery of the first stimulus and delivery of the second stimulus are time-delayed.

14. The method of claim 1, wherein the second target site is the globus pallidus interna.

15. The method of claim 14, further comprising delivering a third stimulus to a subthalamic nucleus.

* * * * *